United States Patent
Van Der Wal

[11] Patent Number: 5,898,752
[45] Date of Patent: Apr. 27, 1999

[54] X-RAY ANALYSIS APPARATUS PROVIDED WITH A DOUBLE COLLIMATOR MASK

[75] Inventor: Hendricus G. M. Van Der Wal, Almelo, Netherlands

[73] Assignee: U.S. Philips Corporation, New York, N.Y.

[21] Appl. No.: 08/959,219

[22] Filed: Oct. 28, 1997

[30] Foreign Application Priority Data

Nov. 5, 1996 [EP] European Pat. Off. .............. 96203078

[51] Int. Cl.$^6$ ................................................ G01N 23/223
[52] U.S. Cl. ................................................ 378/49; 378/45
[58] Field of Search ..................... 378/45–49, 83

[56] References Cited

U.S. PATENT DOCUMENTS 5,408,512   4/1995   Kuwabara et al. ....................... 378/49

FOREIGN PATENT DOCUMENTS

0623817A1   11/1994   European Pat. Off. ..... G01N 23/207

Primary Examiner—Craig E. Church
Attorney, Agent, or Firm—Anne E. Barschall

[57] ABSTRACT

A Soller slit 16 in an X-ray spectrometer can parallelize fluorescent radiation which emanates from a specimen 4 and is to be analyzed according to wavelength by an analyzer crystal 18. Because the aim is to irradiate an as large as possible surface of the specimen 4 by means of primary X-rays 10, inevitably disturbing fluorescent radiation is also generated by the environment of the specimen, for example the specimen holder 6. In order to intercept this disturbing radiation so that it cannot reach the X-ray detector, a collimator mask 12 is arranged in a fixed location in the beam path. In the case of varying specimen dimensions it is not always possible to choose such dimensions for this mask that the disturbing radiation is intercepted. Therefore, a second collimator mask 28 is provided (behind the Soller slit 16) in order to intercept the disturbing radiation in cooperation with the first mask 12.

4 Claims, 2 Drawing Sheets

X-RAY ANALYSIS APPARATUS PROVIDED WITH A DOUBLE COLLIMATOR MASK

The invention relates to an apparatus for X-ray analysis, including a specimen location for accommodating a specimen to be analyzed, an X-ray source for generating X-rays in the specimen, a detector for detecting X-rays emanating from the specimen, an analyzer crystal which is arranged in the beam path between the specimen and the detector, a collimator which is arranged in the beam path between the specimen location and the analyzer crystal in order to parallelize X-rays to be conducted to the analyzer crystal, a collimator mask which is arranged in the beam path between the X-ray source and the collimator.

An apparatus of this kind is known from the published European Patent Application 0 623 817.

Generally speaking, X-rays (fluorescent radiation) are generated in a specimen to be analyzed in an X-ray spectrometer; this radiation is characteristic of the elements and chemical combinations present in the specimen. The fluorescent radiation can be excited in the specimen by X-rays emanating from an X-ray source which is usually an X-ray tube. The fluorescent radiation excited in the specimen has a more or less broad spectrum of wavelengths which are present in the spectrum with a given intensity distribution which is characteristic of the composition of the specimen.

It may occur that the user of an X-ray spectrometer is interested only in the intensity of one wavelength, i.e. one "spectral line". This situation occurs when the content of a given chemical element in the specimen to be analyzed is to be determined. It may also occur that the user is interested in the intensity distribution of the wavelengths. This situation occurs when the content of a number of chemical elements in the specimen to be analyzed is to be found, or when the interaction of these elements is to be determined. Thus, because the intensity of the fluorescent radiation is to be found for one or more wavelengths, the fluorescent radiation must be analyzed according to wavelength. This can be achieved by conducting the fluorescent radiation to an analyzer crystal. This analysis is based on the well-known Bragg relation: $2d \cdot \sin\partial = n\lambda$, where d is the distance between the X-ray reflective crystal faces in the analyzer crystal, $\partial$ is the angle of incidence of the radiation to be analyzed on the analyzer crystal, $\lambda$ is the wavelength of the reflected radiation, and n is an integer. Measurement of the intensity of the radiation which is incident at a given angle 'se relative to the lattice planes of the analyzer crystal and is reflected at the same angle reveals the associated wavelength having this intensity. The intensity of the relevant wavelength can then be measured by means of a customary detector.

Execution of the intensity analysis by means of an analyzer crystal thus requires the incident radiation to form a parallel beam, as otherwise a wavelength would be reflected for each angle of incidence $\partial$ present in the beam, so that it would not be known with which wavelength the intensity observed at the relevant instant is associated. In order to parallelize the X-ray beam incident on the analyzer crystal, a collimator is arranged in the beam path between the specimen and the analyzer crystal. This collimator is constructed, for example as a stack of X-ray absorbing plates wherebetween very small gaps are formed which transmit the radiation, i.e. a so-called Soller slit. This known collimator transmits exclusively X-rays travelling substantially parallel to said plates.

It is to be noted that in this context the term "analyzer crystal" is to be understood to mean not only real crystals, but also multilayer mirrors for X-rays which are known per se. Such a mirror consists of a stack of different, thin layers of comparatively small thickness, for example 2 nm. Such a mirror also enables measurement of long-wave X-rays, as opposed to natural crystals which practically always have a lattice constant, and hence an associated distance of the reflective crystal faces, which is too small for detection of such long-wave X-rays. This limitation of the wavelength to be reflected is also revealed by the above-mentioned Bragg relation.

In order to ensure that an as large as possible share of the X-rays generated in the X-ray tube is incident on the specimen, the exit window of the X-ray tube is preferably arranged as near as possible to the specimen to be analyzed. However, a part of the X-rays applied to the specimen then inevitably strikes the specimen holder. Consequently, fluorescent radiation is also generated in the specimen holder; this radiation may have a disturbing effect on the intensity to be measured. In order to prevent this stray radiation from reaching the detector, an X-ray absorbing mask is provided to intercept the disturbing radiation. This mask is arranged in the beam path between the specimen location and the analyzer crystal, near the collimator, at the specimen side; therefore, this mask is referred to as a collimator mask. The effect of the collimator mask is that only the surface of the specimen is visible from the X-ray detector, so that the disturbing radiation cannot reach the detector. With a view to optimum fluorescent radiation yield, and hence a maximum sensitivity of the measurements, the shape, the dimensions and the location of the opening in the mask are chosen so that as much fluorescent radiation from the specimen as possible is transmitted and that the radiation originating from the specimen holder is blocked at the same time.

The cited European Patent Application 0 623 817 discloses an X-ray spectrometer which is provided with one collimator mask which is arranged between the specimen and the collimator in the form of a Soller slit. This mask is constructed as a slidable plate with a plurality of openings which can be slid into and out of the beam path between the specimen and the Soller slit as desired. Thus, the fluorescent radiation emanating from each time a different desired part of the specimen can be selected by sliding said plate in the known spectrometer.

A problem arises in the known spectrometer when it is desired to use specimen holders of different dimensions and/or detector entrance windows of different dimensions, however, while retaining said optimum yield of fluorescent radiation. This problem will be illustrated with reference to the FIGS. 2a and 2b. These FIGS. show the beam path in a plane extending perpendicularly to the so-called diffraction plane, i.e. a plane extending perpendicularly to the plane of drawing of FIG. 1. This plane is also referred to as the sagittal plane.

FIG. 2a shows diagrammatically the path of the fluorescent radiation generated in the specimen 4, said path extending from a specimen holder 6 in which the specimen is accommodated to an X-ray detector 20. FIG. 2a shows a specimen of given dimensions. The extreme rays 3 and 5 of the beam of fluorescent radiation are shown, that is to say the rays extending from the extreme points of the specimen to the oppositely situated points of the detector window 22. Because a collimator mask 12 is arranged in the beam path, radiation generated by the material of the holder 6, for example the ray 7, is prevented from reaching the detector window; such rays are intercepted by the collimator mask 12.

However, if a specimen of smaller dimensions is used, for example the specimen 4 of FIG. 2b, it appears to be impossible to arrange a collimator mask at the same distance from the specimen so as to stop the radiation emanating from the specimen holder 6. This situation is illustrated by the ray 7 which can always reach the detector window, irrespective of the dimensions of the opening in the collimator mask. This problem cannot be solved by suitable choosing the dimensions of the opening in the collimator mask 12. It would be feasible to solve this problem by moving the location of the collimator mask in the direction of the specimen, but this is an undesirable solution in a spectrometer because the necessary space is absent in most spectrometer designs. It would also be feasible to solve this problem by making the entrance window of the detector smaller; however, this is an undesirable solution because it introduces a loss of measured intensity and hence a deterioration of the signal-to-noise ratio during the intensity measurement.

It is an object of the invention to provide an X-ray analysis apparatus in which, for a number of different dimensions of the specimen, disturbing radiation emanating from the vicinity of the specimen is prevented from reaching the entrance window of the X-ray detector by using comparatively simple technical means.

To this end, the invention is characterized in that the apparatus includes a further collimator mask which is arranged in the beam path between the collimator and the detector.

As will be described in detail hereinafter with reference to the drawings, it has been found that the two collimator masks enable interception of the disturbing radiation emanating from the environment of the specimen and transmission of the fluorescent radiation emanating from the specimen to the detector.

In an embodiment of the invention, both collimator masks are constructed so as to be adjustable. This step enables the undesired disturbing radiation to be intercepted in dependence on the dimensions of the specimen holder, resulting in an optimum ratio of the fluorescent radiation to be detected to the undesirable disturbing radiation.

In a further embodiment of the invention, a mechanical coupling is provided between the two collimator masks for adjustment of the two masks. This method of adjustment is attractive when the apparatus deals with only a limited number of dimensions of specimen holders which are known in advance. Each pair of corresponding mask openings can then be adapted to one of the expected dimensions of the specimen. Moreover, simple adjustment can then be realized by means of a single drive.

In a further embodiment of the invention, each of the two collimator masks is constructed as a rotatable disc provided with a number of mask openings, both discs being mounted on a common shaft. The desired pair of mask openings can thus be adjusted by rotation of the two rotatable discs.

The invention will be described in detail hereinafter with reference to the Figures in which corresponding reference numerals denote corresponding elements; therein:

Figure 1:
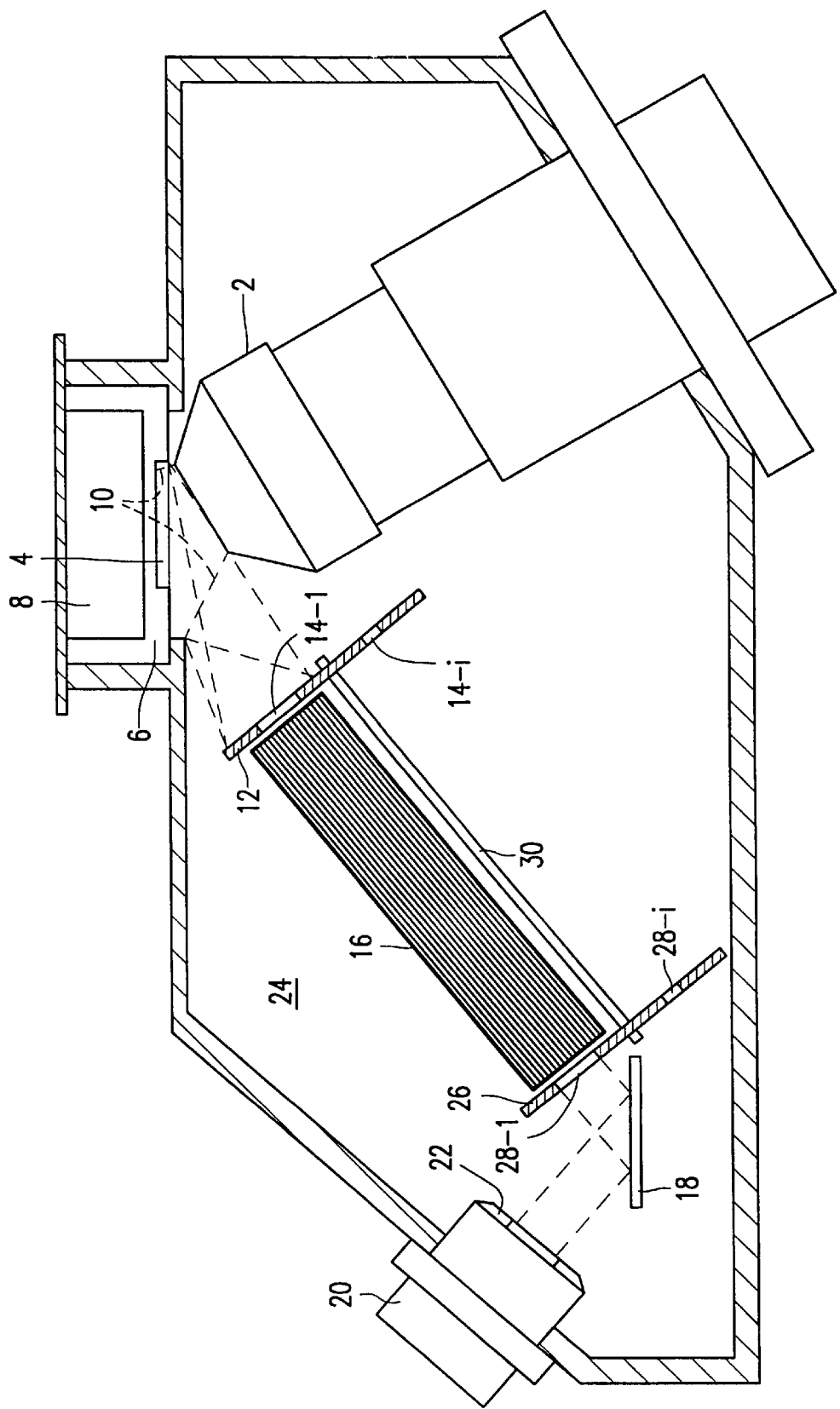
FIG. 1 is a partly sectional view of a part of the X-ray spectrometer which is of relevance to the invention.

FIG. 1 shows a part of an X-ray spectrometer which is of relevance to the invention. The X-ray spectrometer includes an X-ray tube 2 for generating an X-ray beam 10 which irradiates a specimen 4 to be analyzed. To the present invention it is not relevant that the X-ray fluorescent radiation is generated in the specimen by means of X-rays emanating from an X-ray tube; it is also feasible to irradiate the specimen by means of, for example electrons whereby X-rays are generated in the specimen.

The specimen 4 is arranged in a specimen holder 6 in a separate specimen chamber 8. In the specimen X-ray fluorescent radiation is generated which propagates in all directions as denoted by dashed lines in the Figure. Part of the fluorescent radiation enters, via an opening 14 in a first collimator mask 12, a collimator 16 in the form of a known Soller slit. After parallelization of the beam of fluorescent radiation in the Soller slit, it is reflected to the entrance window 22 of an X-ray detector 20 by an analyzer crystal 18. The X-rays thus reflected are detected in the detector 20, after which further signal processing is performed by means of electronic means (not shown).

The beam path from the X-ray tube 2 to the detector 20 extends in a measuring space 24 which can be hermetically sealed and, if desired, evacuated or filled with a gas suitable for the measurements.

In addition to the first collimator mask 12, having a number of mask openings 14-i, there is provided a second collimator mask 26 which preferably has an equally large number of mask openings 28-i. The collimator masks are constructed as rotatable discs in which the mask openings are provided, a mechanical coupling in the form of a common shaft being provided between the two discs. The rotations of the two discs are thus rigidly coupled. The rotation of the two discs 12 and 26 can be realized, if desired, by driving by means of a motor (not shown). Because the choice of the mask opening to be used for a given measurement is determined by the dimensions of the specimen 4 and/or the dimensions of the detector window 22, the angular position of the discs can be determined by a code which is provided on the specimen holder 6 and/or on the detector window 20 and can be automatically read so as to control, the motor (not shown) for adjustment of the angular position of the discs 12 and 26.

Figure 2A:
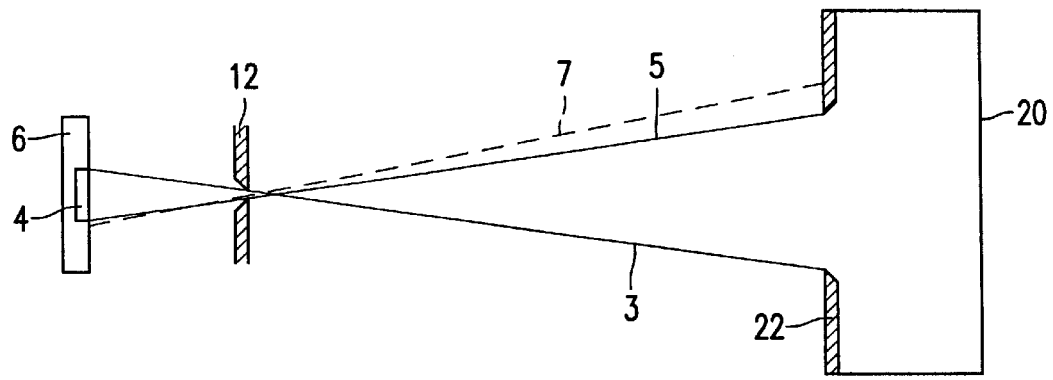
FIGS. 2a, 2b and 2c show diagrammatically the beam path in an X-ray spectrometer so as to illustrate the problem solved by the invention.
Figure 2B:
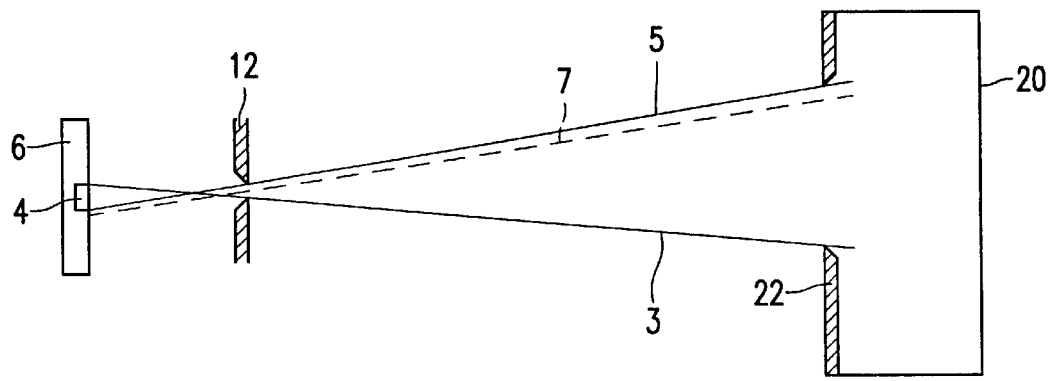

The FIGS. 2a and 2b have already been described for illustration of the problem to be solved by the invention. In these Figures, like in FIG. 2c, the beam path is shown in a plane extending perpendicularly to the so-called diffraction plane, that is to say a plane (the sagittal plane) extending perpendicularly to the plane of drawing of FIG. 1.

Figure 2C:
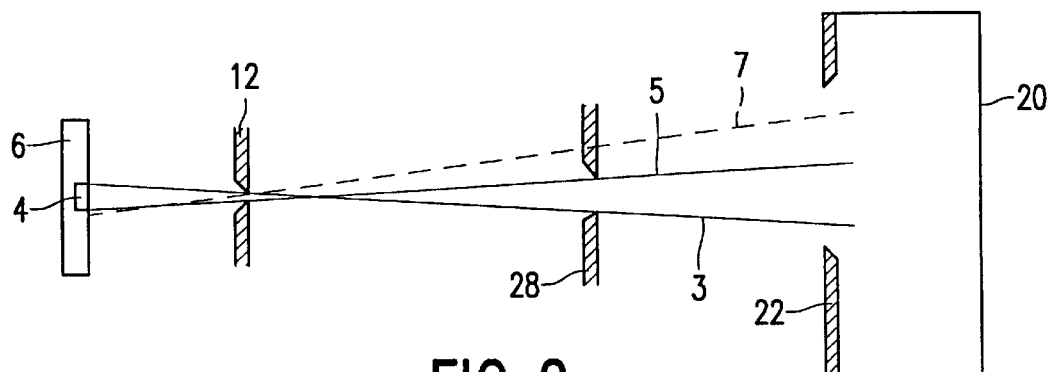

Like the FIGS. 2a and 2b, FIG. 2c shows diagrammatically the beam path of the fluorescent radiation, generated in a specimen 4, from a specimen holder 6 accommodating the specimen to an X-ray detector 20. FIG. 2c shows a specimen having dimensions equal to the dimensions of the specimen in FIG. 2b. The extreme rays 3 and 5 of the beam of fluorescent radiation are shown, i.e. the rays extending from the extreme points of the specimen to the detector window via the limitation openings of the collimator masks 12 and 28 (or the smaller of these two, viewed from the specimen).

In the situation shown in FIG. 2b, the ray 7 could always reach the detector window 22, regardless of the dimensions of the opening in the collimator mask 12. This problem is solved in FIG. 2c by the presence of the further collimator mask 28 which now intercepts the ray 7 and transmits the desired fluorescent radiation.

I claim:

1. An apparatus for X-ray analysis, including:

a specimen location for accommodating a specimen to be analyzed, an X-ray source for generating X-rays in the specimen, a detector for detecting X-rays emanating from the specimen, an analyzer crystal which is arranged in the beam path between the specimen and the detector, a collimator which is arranged in the beam path between the specimen location and the analyzer crystal in order to parallelize the X-rays to be conducted to the analyzer crystal, a collimator mask which is arranged in the beam path between the X-ray source and the collimator. characterized in that the apparatus includes a further collimator mask which is arranged in the beam path between the collimator and the detector.

2. An apparatus as claimed in claim 1, in which both collimator masks are constructed so as to be adjustable.

3. An apparatus as claimed in claim 2, in which a mechanical coupling is provided between the two collimator masks for adjustment of the two masks.

4. An apparatus as claimed in claim 3, in which each of the two collimator masks is constructed as a rotatable disc provided with a number of mask openings, both discs being mounted on a common shaft.

* * * * *